United States Patent [19]
Dupret et al.

[11] Patent Number: 5,869,236
[45] Date of Patent: Feb. 9, 1999

[54] MUTATION DETECTING METHOD USING PHOTOBRIDGING-STABILIZED DOUBLE-STRANDED DNA DENATURING GRADIENT ELECTROPHORESIS

[75] Inventors: Daniel Dupret, Schweighouse-sur-Moder; Michel Goossens, Paris; Marcel Chassignol, Semoy; Thank Thuong Nguyen, Vienne-en-Val, all of France

[73] Assignee: Appligene, S.A., Cedex, France

[21] Appl. No.: 285,931

[22] Filed: Jul. 25, 1994

Related U.S. Application Data

[63] Continuation of PCT/FR93/00020 Jan. 11, 1993.

[30] Foreign Application Priority Data

Jan. 24, 1992 [FR] France .................................. 92 00737

[51] Int. Cl.$^6$ .............................. C12Q 1/68; C12P 19/34
[52] U.S. Cl. ................................................. 435/6; 435/91.2
[58] Field of Search ........................ 435/6, 91.2; 935/77, 935/78; 536/24.3, 24.33, 26.6

[56] References Cited

FOREIGN PATENT DOCUMENTS

| | | |
|---|---|---|
| 0117777 | 9/1984 | European Pat. Off. . |
| 2540122 | of 1984 | France . |
| 92 00737 | 1/1992 | France . |
| WO8902930 | 4/1989 | WIPO . |
| WO9001563 | 2/1990 | WIPO . |
| 9315223 | 5/1993 | WIPO . |

OTHER PUBLICATIONS

Sheffield et al, "Attachment of a 40–base–pair G+C–rich sequence (GC–clamp) to genomuc DNA fragments by the polymerase chain reaction results in improved detection of single–base changes", Proc. Natl. Acad Sciences, vol. 86, pp. 232–236 (Jan. 1989).

Costes et al, Human–Mol–Genet 2:393–397 (1993).

Am. J. Hum. Gent 51(4Supp):A217 (1992).

*Primary Examiner*—W. Gary Jones
*Assistant Examiner*—Eggerton Campbell
*Attorney, Agent, or Firm*—Weiser & Associates, P.C.

[57] ABSTRACT

A method for the detection of nucleic acid sequence variants is disclosed which method comprises the stabilization of a portion of the sequence by a covalent bond with a photo-activatable intercalating agent and compositions.

22 Claims, 4 Drawing Sheets

MUTATION DETECTING METHOD USING PHOTOBRIDGING-STABILIZED DOUBLE-STRANDED DNA DENATURING GRADIENT ELECTROPHORESIS

This application is a continuation of PCT/FR93/00020, filed Jan. 11, 1993, now abandoned, which claims priority to French Application No. 92/00737, filed on Jan. 24, 1992.

The present invention relates to a new method of detection of mutations by electrophoresis on a denaturing gradient gel of double-stranded DNA stabilized by photobridging by means of one or more photoactivatable intercalating agents.

The invention relates particularly to the use of oligonucleotides linked to at least one photoactivatable intercalating agent, capable of forming under irradiation bridging products with complementary nucleic acid sequences, as primers to stabilize the hybrids formed during a genetic amplification process, for the purpose of analyzing these hybrids by delayed electrophoresis on denaturing gradient gel.

The detection of mutations by methods of delay on a denaturing gradient gel relies on the fact that the electrophoretic mobility (speed of migration) of a DNA fragment is different depending on whether the fragment is completely denaturated (single stranded), partially denatured (loop or hairpin), or perfectly paired (double-strand). A double-stranded DNA can be denaturated by elevation of the temperature or denaturating agents like urea or formamide which favor this denaturation by decreasing the melting temperature of the hybrid.

When a double-stranded DNA is subjected to progressive denaturation conditions, there is observed a step-wise denaturation of the hybrid. The progressive denaturation will have as an effect the dissociation of different domains of the double-stranded DNA chain, beginning with the less stable domains until the complete dissociation of the hybrid occurs. It has been shown that the zones rich in pairs of G/C are more stable than the zones rich in pairs of A/T.

The loop or hairpin will therefore appear in unstable domains under the denaturation conditions given.

The electrophoretic migration in an acrylamide gel where there was created a denaturing gradient, e.g., a change of concentration of denaturing agent or a change of temperature, permits the discrimination between a perfect hybrid and an imperfect hybrid which represents a loop of fusion or a hairpin, the first one being denaturated later and migrating further on the gel, because the dissociation of a domain stops or slows down considerably the electrophoretic mobility of a DNA fragment.

The denaturing gradient concomitant with the electrophoresis can be obtained by at least three methods:
- a gradient of temperature along the gel, method called TGGE for "Temperature Gradient Gel Electrophoresis",
- a chemical denaturing gradient along the gel, method called DGGE for "Denaturant Gradient Gel Electrophoresis", (see reference 6),
- a gradient of temperature in time, method called TSGE for "Temperature Sweep Gel Electrophoresis" (Kenji Yoshino et al., Nucleic Acids Research, Vol. 19, No. 11, 3153, 1991).

By performing an electrophoresis on acrylamide gels under increasingly denaturing conditions, it is possible to separate by slowing down the electrophoretic mobility, the fragments showing a denaturation of at least one domain from those which show no denaturation or from those which are completely denaturated, and to identify the precise point of denaturation to a pair of bases (S. G. Fisher, L. S. Lerman, Proc. Natl. Acad. Sci. USA, Vol. 80, pp. 1579–1583, March 1983, Biochemistry); (O. Atree et al., Nature, Vol. 313, February 1985, pp. 495–497).

The principle of these techniques, even though known for a long time, could not have easily been performed until recently, thanks to the appearance of the genetic amplification process, which allows one to easily obtain fragments of DNA which can be analyzed by these techniques. The genetic amplification consists of carrying out a cycle constituted of a hybridization phase, an extension phase and a denaturation phase, and repeating this cycle of hybridization-extension-denaturation, known as PCR or "Polymerase Chain Reaction", a sufficient number of time to increase the quantity of initial DNA fragments in an exponential proportion with respect to the number of cycles used.

The hybridization phase consists of using two oligonucleotide primers, each one complementary to a sequence of about 20 bases located on both sides of the DNA fragment to amplify; the mixture of the two primers with genomic DNA, under the appropriate hybridization conditions, allows each primer to anneal to its complementary sequence on the DNA fragment.

The extension phase consists in causing a DNA polymerase to act for which the (3') ends of the oligonucleotides serve as primers and each strand of the DNA fragment to amplify serves as a template. Each oligonucleotide primer is elongated in the (5')-(3') direction until there is obtained a doubling of the sequence of the fragment which is to be amplified.

The denaturation phase consists in separating by the action of heat the double-stranded hybrid produced from the extension phase before the beginning of the next hybridization phase.

The genetic amplification by PCR allows, because of the technique of delay on denaturing gel, the study of the presence of mutations in the population in a very precise manner, in order to correlate these with the presence of genetic diseases (R. K. Saiki et al., Nature, Vol. 324, 13th Nov., 1986, pp. 163–166); (C. Wong et al., Nature, Vol. 384, 26th Nov., 1987, pp. 384–386).

Indeed, let us suppose a region of the genome susceptible of carrying a mutation knowing its sequence, models of calculation enables one to identify in the DNA fragment one or more domains of successive hybridization and thus to predict their temperature of hybridization (see on this subject, reference 10); it is also possible to predict the influence of mutation even point [mutations] on the temperature of hybridization of the domains in question (see on this subject, reference 10).

Thanks to the genetic amplification by PCR, it is possible, by correctly choosing a pair of oligonucleotide primers, to amplify a DNA fragment containing at least two domains of hybridization and to obtain an important quantity (a couple of hundred nanograms) of this purified fragment. The electrophoretic analysis of this fragment by a chemical or thermal denaturing gradient allows the measurement of the temperature of hybridization of the domain; this varying with the sequence, it is possible to identify the presence of possible mutations on the basis of a different migration in comparison with the control fragment.

An important step of this protocol rests in the choice of specific oligonucleotide primers which flank the hybridization domains which is studied.

Indeed, a nucleotide variation can be detected only if it is located in the first domain of hybridization, that is, the segment which is denaturated first when the fragment meets in the gel, the point where the concentration of denaturant (or the temperature) corresponds to its hybridization temperature (Tm). A mutation is detectable by this method only if a second domain exists, which is more stable than the first one and if the mutation is localized in the first domain of hybridization. In order to position the DNA sequence which is explored in the first domain of hybridization in a systematic manner, it is proposed in the prior art to analyze the sequence of the duplex of DNA with the help of appropriate algorithms in order to determine the position of the amplification primers, and to stabilize one of the termini of the fragment analyzed by introducing, with the help of modified oligonucleotide primers, a GC tail of at least 40 bases, also called "GC clamp". The introduction of this GC clamp creates a domain resistant to denaturation, which causes the less stable domain(s) to be analyzable for the mutations that it contains.

It is proposed in the prior art to stabilize one of the termini of the amplified fragment with the help of oligonucleotide primers modified by introducing in position (5') a GC tail (Kenji Yoshino et al., Nucleic Acids Research, Vol. 19, No. 11, 3153, 1991) (see also on this subject reference 15).

This model is currently used by laboratories for the diagnosis of mutations in the genes of beta globin, of factors IX and VIII of the coagulation, and of the mucoviscidosis gene (see on this subject, reference 2, 4, 7, 8, 9, 16, 17).

However, the synthesis of GC clamp is difficult to realize because the deoxyguanine (represented by the letter G), which is a purine, is also the nucleoside the most unstable under the reaction conditions used in the synthesis of oligonucleotides. Indeed, during each cycle of the phosphoramidites coupling during the synthesis of the oligonucleotide, detritylation in an acid milieu (by TCA) is done, and, at the end of the synthesis, a basic treatment using warm ammonia is carried out to unprotect the bases. There is then observed that a large portion of the oligonucleotides, particularly when they contain many G residues, are truncated exactly at the G because of a depurination.

The GC clamps used in these techniques are often very long and can in some cases attain 60 to 80 bases. Their synthesis is therefore difficult, involving a considerably higher cost in the preparation of oligonucleotide primers.

In addition, GC clamps are not always stable enough to avoid the opening of the terminus before the melting of the domain, and in consequence does not allow the study of some of the domains of hybridization.

The present invention aims to provide a new means of stabilization of at least one of the termini of the DNA fragment of interest, without the inconveniences of the GC clamp. This goal is attained according to the invention by replacing the GC clamp by the introduction of at least one covalent bond linking the two strands of DNA at the terminus to be stabilized.

The French Patent Application published under the No. 2,540,122 describes as new chemical compounds, an oligonucleotide sequence linked to an intercalating agent. These chemical compounds anneal to any complementary oligonucleotide sequences in a selective manner. The presence of an intercalating agent which possess a strong affinity for the stacked bases permits to stabilize the hybrid formed which, however, can be dissociated. Furthermore, the presence of intercalating agents having properties distinct from the nucleotides allows their detection.

The intercalating agents proposed in the patent application mentioned above are compounds known in art dealing with nucleic acid; in general it concerns, polycyclic compounds having a planar configuration such as acridine, furocoumarine or ellipticine and their derivatives.

Among these, psoralene (or furocoumarine) and its derivatives, designated hereafter as photoactivatable intercalating agents, besides their capacity to intercalate between the stacked bases of the two strands of DNA, have also the property of forming covalent bonds between the double bond 3,4 of the pyrone ring or 4',5' of the furan ring, with the 5,6 double bond of pyrimidines bases, in particular thymidine, under irradiation at about 360 nm.

Accordingly, the photoactivatable intercalating agent coupled to an oligonucleotide by the intermediary of an adequate carbon arm, as is described in French Patent Application No. 2,540,122, will intercalate itself between the stacks of bases formed by the oligonucleotide and any complementary nucleic acid sequence; the irradiation at 360 nm of the hybrids obtained will allow the creation of covalent bonds between the intercalating agent so activated and the complementary nucleic acid sequence in a manner to create a stable bridging hybrid.

Also known is International Patent Application published under the No. WO 90/12020 which propose to couple a furocoumarine to an oligonucleotide by the intermediary of a ribose sugar or deoxyribose.

The European Patent Applications No. 316,016, International No. WO 89/06702 and German No. 3,928,900 describe the use of conjugates of psoralen and oligonucleotides to block the genetic expression.

French Patent Application No. 2,568,254, describes the application of oligonucleotide compounds linked to an intercalating agent to selectively block a nucleic acid sequence, and more particularly, the application of these compounds for the selective blockage in vivo of the expression of a gene or of a sequence implicated in the initiation, propagation or termination of the replication of a nucleic acid, or of the transcription of one or more genes and/or their translation.

Applicant has now shown that oligonucleotides linked to at least one photoactivatable intercalating agent, such as psoralen or its derivatives, can be used as primers in the process of PCR genetic amplification in vitro, and that the hybrids so obtained were, after photobridging, perfectly stabilized to be studied by delayed electrophoresis on denaturing gradient gel.

Accordingly, the invention relates to a process of detection of mutation by electrophoresis of double-stranded DNA in gradient denaturing gels, characterized by the fact that the hybrid analyzed is stabilized by photobridging by means of one or more photoactivatable intercalating agents.

According to the process of this invention, the hybrid analyzed is obtained by a genetic amplification process of a double-stranded DNA fragment, for which the hybridization phases are performed with two oligonucleotide primers, at least one of which contains at its 5' terminus, one or more photoactivatable intercalating agents.

After the genetic amplification process by PCR, the irradiation of the hybrids at about 360 nm allows the creation of covalent bonds between one or more intercalating agents so activated and the pyrimidine bases, in particular the thymidines, which are found in the immediate vicinity on the complementary strand. These covalent bonds ensure a stable bridging between the DNA strand carrying at least one photoactivatable intercalating agent and the DNA strand template to which the bridging was realized.

The combination constituted of an oligonucleotide primer onto which is fixed at least one photoactivatable intercalating agent responds to the following formula:

in which:

the radicals B can be identical or different and represent each one a nucleic acid base;

Y represents an alcoylene radical straight or branched —alk— or a radical:

$$-alk-NH-\overset{O}{\underset{\|}{C}}-;\quad -alk-O-\overset{E}{\underset{\|{O}}{P}}-;$$

The radicals E can be identical or different and represent each one an oxoanion O—, a thioanion S—, a alcoxy group, or a —O—alk—Z group; and m is a whole integer comprised between 1 and 5.

Z is a radical corresponding to a photoactivatable intercalating agent, being able to form photobridging with pyrimidine bases.

n is a whole integer number comprised between 2 and 150.

It should be noted that the formula I represents a series of nucleotides, the sequence of which is complementary to a sequence of 15 to 30 bases located at the 3' terminus of the DNA fragment to amplify; n indicating simply the number of nucleotides comprised in the molecule; n is a number comprised between 2 and 150 and in preference between 10 and 30.

The photoactivatable intercalating agents Z which are able to form photobridging with the pyrimidine bases, are compounds known in techniques relating to nucleic acids, and concerns compounds able to "intercalate" themselves into the structure of DNA or of double helix RNAs, or hybrids of DNA-RNA, and to form bridging products with the pyrimidine bases under irradiation.

These intercalating agents are, in general, polycyclic compounds having a planar configuration and possessing photoactivatable double bonds, or an azido-$N_3$ group. Among these compounds, one can cite for example, the derivatives of 8-methoxypsoralen, of 5-methoxypsoralen, of 4'-hydroxymethyl-4,5',8-trimethylpsoralen, of 3-carbethoxypsoralen, of angelicine, of pyrido(3,4-c) psoralen, of pyrido(3,4-c)8-methylpsoralen.

Among the meanings for Z, two will be used more particularly:

the oxy-8-psoralen group, the oxy-5-psoralen group.

These compounds can be prepared by processes which are already known (F. Eckstein. In Oligonucleotides an analogues: a practical; Oxford University Press (1991), pp. 283–308) in particular by the synthesis process called "phosphoramidite".

In the formula (I), there is used the condensed representation of nucleotides as follows:

which corresponds to the developed formula:

on which the 5' and 3' termini are designated.

According to a first mode of realization, it is preferred in formula I that the radical B located at the 5' terminus of the oligonucleotide primer be an adenine (A). According to a second mode of realization, there is preferred in formula I that at least two of the successive radicals B located at the 5' terminus of the oligonucleotide be adenines.

Indeed, the irradiation of the hybrid obtained after amplification, will allow to create covalent bonds between the intercalating agent thus activated and the thymidines (T) which are located in the immediate vicinity on the complementary strand.

In an advantageous manner, the radical Z is chosen among the oxy-8-psoralen and oxy-5-psoralen group.

According to a preferred mode of practice of the process of the invention, one only of the oligonucleotide primers is conjugated to one photoactivatable intercalating agent.

The detection process of mutation according to the invention consists first of conducting a genetic amplification of the DNA fragment to analyze, in which the hybridization phases are carried out with two oligonucleotide primers, on at least one of which, there is fixed one or more photoactivatable intercalating groups, and then to subject the hybrids obtained to an irradiation and then that possible mutations are detected by comparing the result of delayed electrophoresis on gradient denaturing gel of the hybrids previously irradiated with the electrophoresis under the same condition than a control sample without any mutation or containing a known mutation.

The delayed electrophoresis on gradient denaturing gel is done preferably according to a temperature gradient or chemical denaturing gradient or a temperature gradient over time.

The invention has also for object the application of an oligonucleotide at the (5') extremity of which there is fixed at least one photoactivatable intercalating agent, for the genetic amplification of a DNA fragment, for which the (3') extremity of the oligonucleotide is used as a primer for a DNA polymerase.

The invention has also for objective the application of a hybrid stabilized by photobridging by means of at least one photoactivatable intercalating agent, for the detection of mutations by delayed electrophoresis on gradient denaturing gel, on which the hybrid has been prepared by a process of genetic amplification of a double-stranded DNA fragment for which the hybridization phases are preformed with two oligonucleotide primers, on at least one of which there is fixed at least one photoactivatable intercalating agent.

Beyond the characteristics which preceded, the invention involves others characteristics which will appear during the description which follows and which refers to examples of realization and of practice of the present invention, it is being understood that these examples would not constitute any kind of limitation to the scope of claims.

I—PREPARATION OF THE PRIMERS

The following example concerns the genetic amplification by PCR of a part of exon 10 of the gene of mucoviscidosis (CFTR). There are use for primers, the two oligonucleotides of 20 bases each, with these sequences:

Primer 1: d-(5')-GAACTGGAGCCTTCAGAGGG(3')
Primer 2: d-(3')-GCAGTAGTTTCGTACGGTTG(5')

The two complementary primers of a short sequence located at the 3' end of the DNA strands corresponding to the studied portion of exon 10 and are made to hybridize with the aforesaid fragment. The 3' OH termini of the oligonucleotides are used as primers for one DNA polymerase; each strand of the fragment is used as a template for the enzyme which synthesizes the complementary strands.

The sequence of the portion of the exon 10 studied is indicated here below framed by the two oligonucleotide primers.

d - ( 5 ' ) GAACTGGAGCCTTCAGAGGGTAAAATTAAGCAC
d-(3')CTTGACCTCGGAAGTCTCCCATTTTAATTCGTG
A G T G G A A G A A T T T C A T T C T G T T C T -
CAGTTTTCCTGGA
T C A C C T T C T T A A A G T A A G A C A A G A G T -
CAAAAGGACCT
T T A T G C C T G G C A C C A T T A A A G A A A A T A T -
CATCTTTGGT
A A T A C G G A C C G T G G T A A T T T C T T T T A T -
AGTAGAAACCA
G T T T C C T A T G A T G A A T A T A G A T A C A -
GAAGCGTCATCAA
C A A A G G A T A C T A C T T A T A T C T A T G T C T T C
GCAGTAGTT
AGCATGCCAAC(3')
TCGTACGGTTG(5')

To stabilize the hybrids formed after n hybridization-extension-denaturation cycles of the PCR process, there is used in the prior art a GC clamp of 40 bases grafted at the 5' terminus of primer 1.

This GC tail presents, for example, the following sequence:

The invention proposes to replace this GC tail by a oxy-5-psoralen group; which is coupled to a 5' extremity of the primer 1 by the intermediary of a hexyl-phosphodiester group of formula:

In order to favor, during the irradiation, the formation of covalent bonds between the psoralen and the two nucleotides TT complementary to the AA nucleotides of the primer 1, the first nucleotide G in (5') of this primer 1 is deleted.

II—GENETIC AMPLIFICATION BY PCR

The following study aims to show on one hand, that the presence of psoralen on primer 1 does not disturb the amplification process, and that a unique strand is correctly synthesized and on the other hand, the efficacy of the photobridging.

1) Amplification

| Reaction mixture: | |
|---|---|
| genomic DNA | 250 ng |
| Primer 1 | 400 pmoles |
| Primer 2 | 400 pmoles |
| dATP | 0.4 mM |
| dGTP | 0.4 mM |
| dCTP | 0.4 mM |
| dTTP | 0.4 mM |
| Tris HCl pH 9 | 50 mM |
| KCl | 50 mM |
| (NH₄)₂SO₄ | 16 mM |
| MgCl₂ | 7 mM |
| BSA | 0.2 mg/ml |
| Taq DNA polymerase | 2.5 U |
| H₂O | QSP 400 µl |

The reaction mixture is covered with paraffin, then placed in a programmable incubator and undergoes the following cycles:

| | |
|---|---|
| 1 minute at 93° C. | |
| 1 minute at 60° C. | |
| 1 minute at 70° C. | x29 |
| 1 minute at 91° C. | |
| 1 minute at 60° C. | |
| 10 minutes at 70° C. | | then the paraffin is removed.

2) Irradiation

100 µl of amplification product is deposited on a glass sheet. The irradiation is carried out with a UV lamp type Vilber Lourmac VL-4LC (365 nm) located at 5 mm above the sample, for 12 minutes.

3) Analysis of amplification and irradiation products a) Analysis on non denaturing polyacrylamide gel 10 µl of non irradiated amplification product and 10 µl of irradiated amplification product are deposited with a marker sample of molecular weight (pBR 322/Hae III) on a 8% acrylamide gel.

Figure 1:
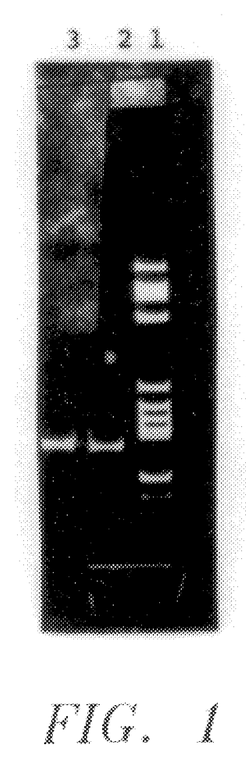
FIG. 1 shows the results of electrophoresis. Lane 1 is a marker of molecular weight standards. Lane 2 is a non-irradiated amplification product. Lane 3 is an irradiated amplification product.

FIG. 1 represents the result of electrophoresis, after treatment of the gel with ethidium bromide:

lane 1 corresponds to the marker of molecular weight (pBR 322/Hae III) standards.

lane 2 corresponds to the non irradiated amplification product.

lane 3 corresponds to the irradiated amplification product.

In lanes 2 and 3 there is observed a single lane of approximately 150 pair bases. This result indicates that the amplification is not disturbed by the psoralen and furthermore no other degradation of the irradiated fragment took place.

b) Analysis on Polyacrylamide gel in denaturing conditions

The analysis is performed on 8% polyacrylamide gel, urea 8M, electrophoresis maintained by a thermostat at 50° C.

Figure 2:
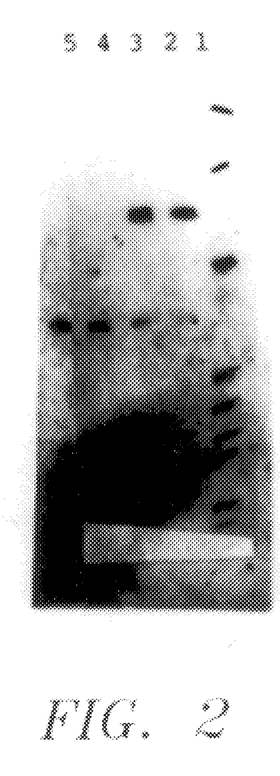
FIG. 2 shows the results of electrophoresis. Lane 1 is a marker of molecular weight standards. Lane 2 is an irradiated sample which has been denatured. Lane 3 is an irradiated sample which has not been denatured. Lane 4 is a non-irradiated sample which has been denatured. Lane 5 is a non-irradiated sample which has not been denatured.

The result of the electrophoresis is represented in FIG. 2:

lane 1 corresponds to a sample of a marker of molecular weight (pBR 322/Hae III).

lane 2 corresponds to a sample of 10 µl of irradiated sample, denaturated at 100° C. for 5 minutes before loading.

lane 3 corresponds to a sample of 10 µl of the irradiated sample nondenaturated.

lane 4 corresponds to a sample of 10 µl of nonirradiated sample, denaturated at 100° C. for 5 minutes before loading.

lane 5 corresponds to a sample of 10 µl of non irradiated and non denaturated sample.

It is noted that the amplification product subjected to irradiation is not degraded, and that 80 to 90% of the DNA fragment presents a molecular weight double that of the non-irradiated fragment; which indicates that the bridging at the 5' terminus of the irradiated fragment generates a single strand of DNA of a size double that of the DNA fragment completely paired.

III—EXAMPLES OF MUTATION DETECTION ACCORDING TO THE PROCESS OF THE INVENTION

1) Analysis of a 3 base pair deletion

Figure 3:
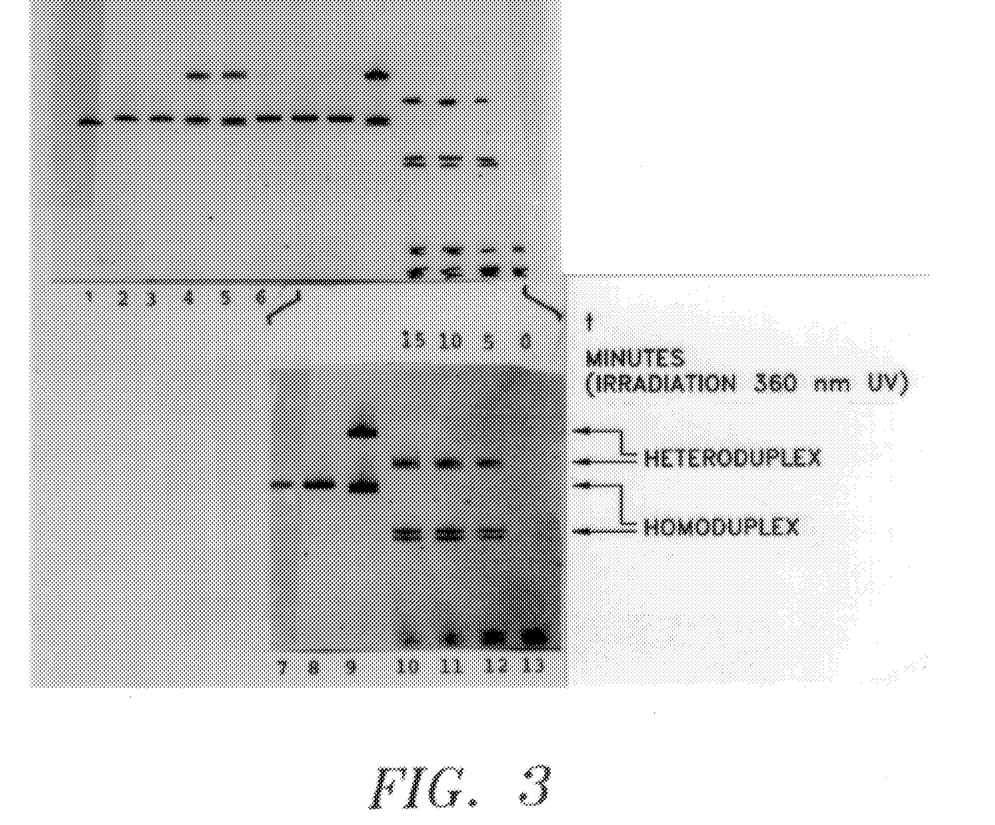
FIG. 3 shows the results of comparative analysis in denaturing gradient gel electrophoresis of a normal DNA sample and a mutant sample. Samples were stabilized either by GC clamp or by psoralen. Samples stabilized by psoralen were either irradiated or non-irradiated.

FIG. 3 represents the results of a comparative analysis in DGGE (denaturation gradient at 10% and 60%) of normal DNA samples (N1) and a mutation (ΔF 508) within exon 10 of the gene CFTR (mucoviscidosis), using to stabilize the hybrid, either a GC tail or psoralen, in the latter case, the psoralen is linked to the 5' terminus of the nucleic acid by an intermediary arm constituted of 6 methylene groups $(CH_2)_6$, this structure is noted: Pso-m6,5'→3'.

The denaturing gradient of 10% and 60% is generated from a 80% stock solution of the denaturant having the following composition: 32% formamide, 5.6M urea in TAE 1X (TAE 1X=Tris 40 mM, sodium acetate 20 mM, EDTA 1 mM, pH 7.4). The acrylamide concentration is 6.5% (acrylamide/bisacrylamide: 37.5/1). The migration time is 3 hours, and the voltage applied is 160 V.

lane 1 corresponds to a sample containing variant DNA ΔF 508; stabilization of the hybrids by GC clamp.

lanes 2, 3, 6, 7 and 8 correspond to samples containing normal DNA N1; stabilization of the hybrids by GC clamp.

lanes 4, 5 and 9 correspond to samples containing the two species N1 and ΔF 508, in equal proportion; stabilization of the hybrids by GC clamp.

lanes 10, 11 and 12 correspond to samples containing the two species N1 and AF 508, each in equal proportion; stabilization of the hybrids by psoralen after irradiation at 360 nm for, respectively 15, 10 and 5 minutes.

lane 13 corresponds to a sample containing the two species N1 and ΔF 508, in equal proportion; stabilization of the hybrids by psoralen without irradiation of the sample.

With the stabilization by psoralen, comparable results are observed to those obtained using the stabilization conditions of the prior art with the GC clamp. A good separation of the homoduplex and heteroduplex exists, which allows an indisputable discrimination between the two variants (normal allele in comparison to mutant allele ΔF 508). Only the migration distance varies in relation to the origin. It is noted that 80% and 90% of the DNA fragment is modified after an action of irradiation at 360 nm.

2) Analysis of a point mutation

Figure 4:
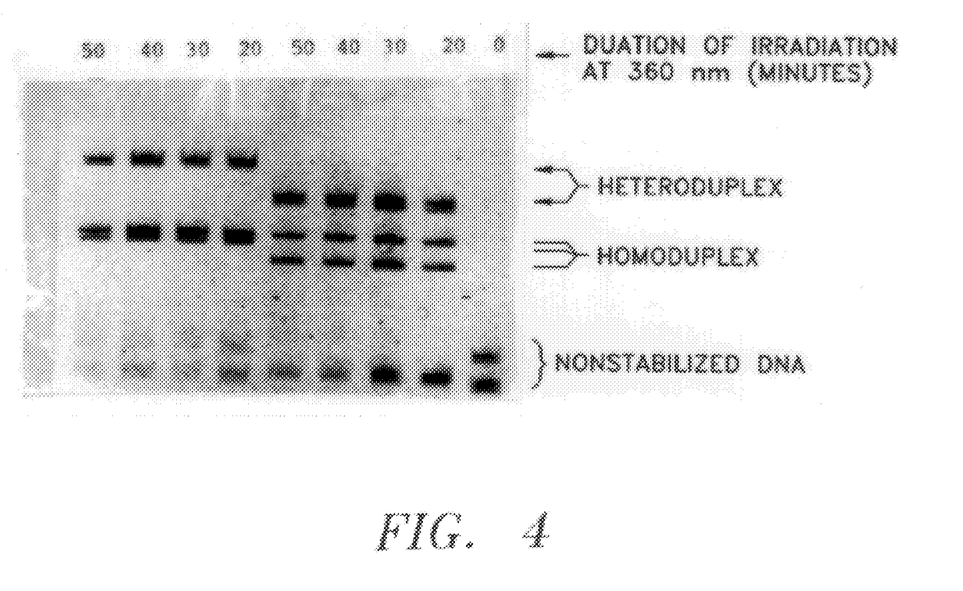
FIG. 4 shows the results of DGGE analysis of normal and of variant DNA stabilized by psoralen.

FIG. 4 represents the results of an analysis in DGGE (denaturing gradient 10 to 60%, composition of the gradient identical to the one used for the analysis of the deletion of 3 base pairs described previously; 160 V for 3 hours) of normal (N1) and variants (ΔF 508 and I506 V) samples for the exon 10 of the gene CFTR (mucoviscidosis), by using the psoralen (Pso-m6, 5'→3') to stabilize the hybrid.

The variant I506 V correspond to the substitution of one nucleotide (nt 1648 A→G) in exon 10 of CFTR.

In this experiment, the DNA was amplified by PCR using primers, one of which contains an photoactivatable intercalating agent, the psoralen, and is developed after amplification to variable times of irradiation at 360 nm.

lanes 1 to 4 correspond to samples containing in equal proportion the two species N1 and ΔF 508, stabilization of the hybrids by psoralen after irradiation of the sample at 360 nm, respectively, for 50, 40, 30 and 20 minutes.

lanes 5 to 9 correspond to samples containing in equal proportion the two species N1 and I506 V, in equal proportion; stabilization of the hybrids by psoralen after irradiation at 360 nm, respectively, for 50, 40, 30 and 20 minutes.

It is observed that a substitution of one nucleotide (nt 1648 A→G in exon 10 of CFTR), which is present in a human DNA sample in an heterozygote state is detectable easily by the presence of homoduplex migrating differently and of heteroduplex.

Figure 5:
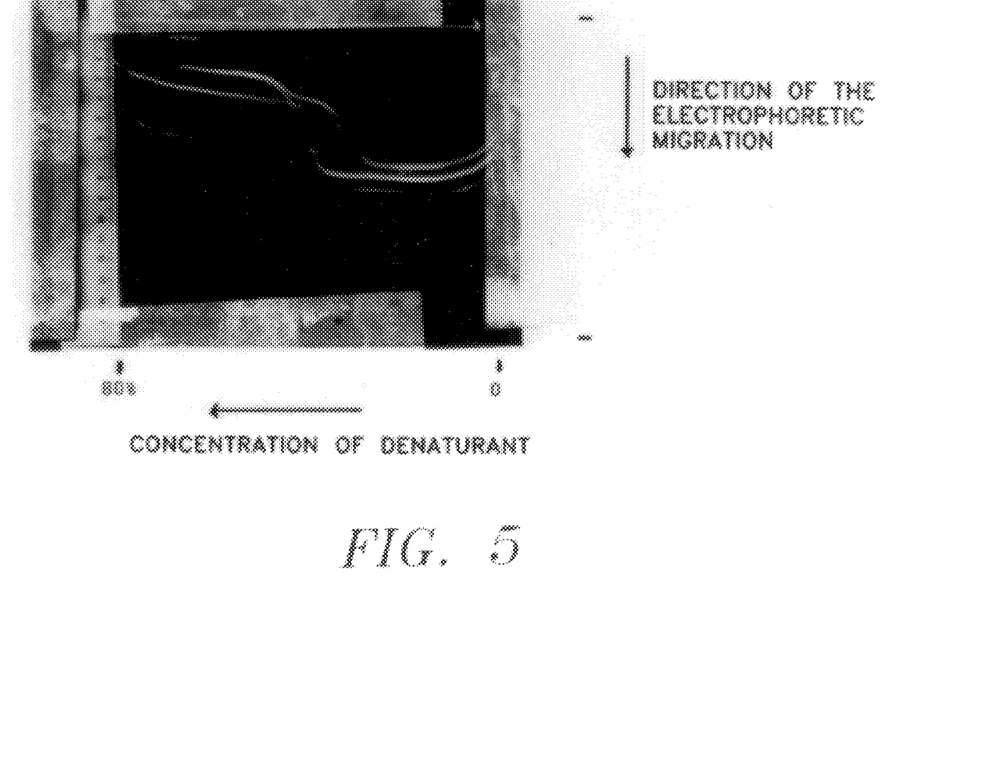
FIG. 5 shows the results of DGGE of normal and variant DNA stabilized by psoralen or by GC clamp.

3) Comparative analysis in an electrophoresis system perpendicular to the denaturing gradient FIG. 5 represents the analysis of two samples containing each in equal proportions species N1 and Δ508, in a perpendicular electrophoresis system of the denaturing gradient of 0 to 80%, one of them is first amplified in presence of a primer containing a GC tail, the other is amplified with a primer coupled to a psoralen.

Figure 6:
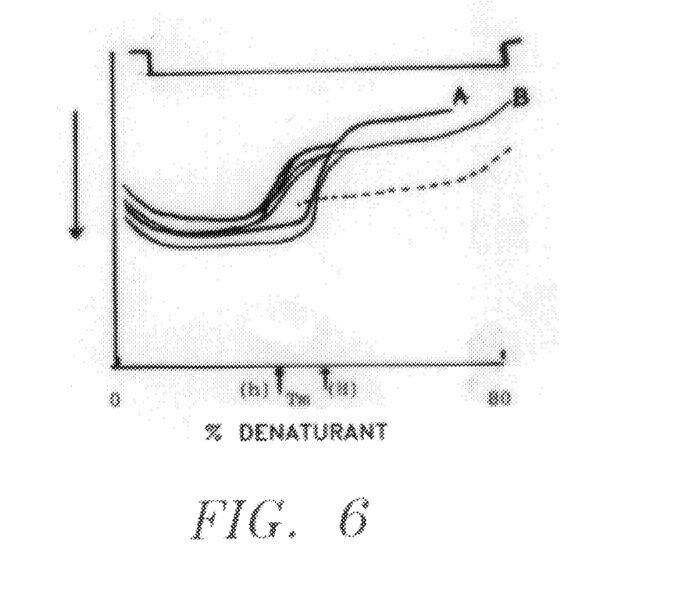
FIG. 6 shows hybridization curves obtained on DGGE of amplified DNA samples stabilized by GC clamp or by psoralen or not stabilized.

In FIG. 6, A represents the fusion curve of the amplified DNA sample in presence of a GC tail, and B, the hybridization curve of a DNA amplified sample with a primer coupled to a psoralen; the dash line corresponds to a non stabilized DNA.

It is observed that the fusion curves of the two samples, if not superimposable present the same aspect. Especially, the temperature (Tm) for which 50% of the sequences are denaturated are very close whether for the homoduplex (H) a heteroduplex (h).

REFERENCES

1) Abrams E S, Murdaugh S E, Lerman, L S; Genomics 1990; 7: 463–475
2) Attree O, Vidaud, D, Vidaud M, Amselem S, Lavergne J, Goosens M; Genomics 1989; 4: 266–272.
3) Burmeister N, Disibio G, Cox D R, Myers R M; Nucl. Acids Res. 1991; 19(7) : 1475–1480.
4) Devoto M, Ronchetto P, Fanen P, et al.; Am. J. Hum. Genet. 1991.
5) Fisher S G, Lerman L S; Cell 1979; 16 : 191.
6) Fisher S G, Lerman L S; Proc. Natl. Acad. Sci 1983; 80 1579.
7) Goosens M, Fanen P, Attree O, Vidaud M; Ann. New York Acad. Sci. 1990;. 612 : 74–80.
8) Kogan S C, Gitschier J; Blood 1988; 72 : 300 a.
9) Kogan S C, Gitschier J; Proc. Natl. Acad. Sci. USA 1990; 87(march) : 2092–2096.
10) Lerman L S, Silverstein K. In : Wu R, ed. Methods in Enzymology. New York; Academic Press 1987 : 482–501, vol. 155.
11) Myers R M, Lumelsky N, Lerman L, Maniatis T; Nature 1985; 313 : 495–498.
12) Myers R M, Fisher S G, Lerman L S, Maniatis T; Nucl. Acids Res. 1985; 13 : 3131–3145.
13) Myers R M, Fisher S G, Lerman L S, Maniatis T; Nucl. Acids Res. 1985; 13 : 3111.
14) Myers R M, Sheffield V C, Cox D R. In : Ehrlich H A, ed. PCR technology : Principles and applications for DNA amplification. New York Stockton Press, 1989 : 71–88.
15) Scheffield V C, Cox D R, Lerman, L S, Myers R M; Proc. Natl. Acad. Sci. USA, 1989; 86 : 232–236.
16) Traystman M D, Higuchi M, Kasoer C, Antonarakis S E, Kazazian H H; Genomics 1990; 6 293–301.
17) Vidaud M, Fanen P, Martin J, Ghanem N, Nicolas S, Goossens M; Hum. Genet. 1990; 85(4) : 446–449.
18) Weber C K, Shaffer D J, Sidman C L; Nucl. Acids Res. 1991; 19(12) : 3331–3335.

We claim:

1. A method for detecting base mutations in a nucleic acid sample comprising subjecting a double-stranded hybrid which has been stabilized by covalent photobridging with a photoactivatable intercalating agent, to denaturing gradient gel electrophoresis and comparing the electrophoresis of the sample to that of a control.

2. The method of claim 1, wherein the double-stranded hybrid is obtained by a process of genetic amplification of a double-stranded DNA fragment, for which the hybridization phases are performed with two oligonucleotide primers, on at least one of which there is fixed one or more photoactivatable intercalating agents.

3. The method of claim 2, wherein a group constituted of the oligonucleotide primer onto which is fixed one or more photoactivatable intercalating agents has the formula:

in which:

The radicals B can be identical or different and represent each one a nucleic acid base Y represents a right alkylene radical straight or branched —alk— or a radical:

The radicals E can be identical or different and represent each one an oxoanion O—, a thioanion S—, a alcoxy group, or a —O—alk—Z group; and m is a whole integer number comprised between 1 and 5;

Z is a radical corresponding to an photoactivatable intercalating agent, being able to form photobridging with pyrimidine bases;

n is a whole integer number comprised between 2 and 150.

4. The method of claim 3, wherein the radical Z is a polyclique compound having a plane configuration and containing photoactivatable double bonds, or an azido-$N_3$ group.

5. The method of claim 4, wherein the radical Z is chosen between the derivatives of 8-methoxypsoralen, of 5-methoxypsoralen, of 4'hydroxymethyl-4,5',8-trimethylpsoralen, of 3-carbethoxypsoralen, of angelicine, of pyrido(3,4-c)psoralen, of pyrido(3,4-c)8-methylpsoralen.

6. The method of claim 4, wherein the radical Z is an oxy-8-psoralen group or an oxy-5-psoralen group.

7. The method of claim 6, in which n is a whole integer between 10 and 30.

8. The method of claim 7, wherein in the formula (I) the radical B located at the extremity (5') of the primer oligonucleotide is an adenine.

9. The method of claim 7, wherein in formula (I) at least two of the successive radical B located at the extremity (5') of the primer oligonucleotide are adenines.

10. The method of claim 9, characterized by the fact that one only of the primer oligonucleotide is conjugated to one or more photoactivatable intercalating agents.

11. The method of claim 1, wherein a genetic amplification of the DNA fragment to be analyzed is performed, for which the hybridization phases are carried out with two oligonucleotide primers, on at least one of them is fixed one or more photoactivatable intercalating agents, thereafter in that the hybrids are subjected to an irradiation, and in that possible mutations are detected by comparing the result of the electrophoresis on a denaturing gradient gel of the aforesaid hybrids previously irradiated with the electrophoresis under the same conditions of a DNA control sample devoid of mutation or containing a known mutation.

12. The method of claim 11, wherein the electrophoresis on denaturing gradient gel is performed according to a temperature gradient or a chemical denaturing gradient or a temperature gradient over time.

13. The method of claim 1 which further comprises, before subjecting the hybrid to denaturing gradient gel electrophoresis, hybridizing the nucleic acid with two oligonucleotide primers on at least one of which there is fixed one or more photoactivatable intercalating agents, thereby obtaining a double-stranded hybrid of the sample and stabilizing the hybrid by photobridging with a photoactivatable intercalating agent.

14. The method of claim 1, wherein the photoactivatable intercalating agent is psoralen or a derivative thereof which forms covalent bonds with the complementary nucleic acid sequence.

15. The method of claim 1 wherein the denaturing gradient gel electrophoresis is performed by a temperature gradient, a chemical gradient, or a temperature gradient over time.

16. A method for detecting base mutations in a nucleic acid sample comprising stabilizing a double-stranded hybrid of the sample by covalent photobridging with a photoactivatable intercalating agent, subjecting the double-stranded hybrid to denaturing gradient gel electrophoresis, and comparing the electrophoresis of the sample to that of a control.

17. The method of claim 16 wherein the nucleic acid sample is a PCR amplified nucleic acid sample.

18. A denaturing gradient electrophoresis gel composition which contains an annealed nucleic acid hybrid stabilized by covalent photobridging with a photoactivatable intercalating agent which hybrid has been subjected to electrophoresis on the denaturing gradient electrophoresis gel.

19. The gel composition of claim 18 wherein the photoactivatable intercalating agent is psoralen.

20. The gel composition of claim 18 wherein the photoactivatable intercalating agent is selected from the group consisting of 8-methoxypsoralen, 5-methoxypsoralen, 4'-hydroxymethyl-4,5',8-trimethylpsoralen, 3-carbethoxypsoralen, angelicine, pyrido(3,4-c)psoralen, and pyrido(3,4-c)8-methylpsoralen.

21. The gel composition of claim 18 wherein the ovalent photoactivatable intercalating agent is an oxy-8-psoralen or an oxy-5-psoralen.

22. The gel composition of claim 19 which is stained with ethidium bromide.

\* \* \* \* \*